(12) United States Patent
Yi et al.

(10) Patent No.: US 8,374,415 B2
(45) Date of Patent: Feb. 12, 2013

(54) SHAPE MODELING AND DETECTION OF CATHETER

(75) Inventors: Sheng Yi, Raleigh, NC (US); Terrence Chen, Princeton, NJ (US); Peng Wang, Princeton, NJ (US); Dorin Comaniciu, Princeton Junction, NJ (US)

(73) Assignee: Siemens Corporation, Iselin, NJ (US)

( * ) Notice: Subject to any disclaimer, the term of this patent is extended or adjusted under 35 U.S.C. 154(b) by 205 days.

(21) Appl. No.: 13/079,846

(22) Filed: Apr. 5, 2011

(65) Prior Publication Data

US 2011/0288404 A1 Nov. 24, 2011

Related U.S. Application Data

(60) Provisional application No. 61/346,196, filed on May 19, 2010.

(51) Int. Cl.
*G06K 9/00* (2006.01)
*A61B 6/02* (2006.01)

(52) U.S. Cl. .......................... 382/131; 382/274; 378/42

(58) Field of Classification Search .................. 382/100, 382/103, 106–107, 128–134, 162, 168, 173, 382/181, 203, 224, 232, 254, 274, 276, 305, 382/312; 378/4, 21, 98.12, 42; 128/899; 600/424

See application file for complete search history.

(56) References Cited

U.S. PATENT DOCUMENTS

| | | | | |
|---|---|---|---|---|
| 5,749,835 A | * | 5/1998 | Glantz | 600/424 |
| 5,944,022 A | * | 8/1999 | Nardella et al. | 128/899 |
| 7,283,614 B2 | * | 10/2007 | Nakano et al. | 378/98.12 |
| 7,792,342 B2 | * | 9/2010 | Barbu et al. | 382/128 |
| 7,801,342 B2 | * | 9/2010 | Boese et al. | 382/128 |
| 2005/0251028 A1 | | 11/2005 | Boese et al. | |
| 2006/0285638 A1 | | 12/2006 | Boese et al. | |
| 2008/0249395 A1 | | 10/2008 | Shachar et al. | |
| 2009/0062641 A1 | | 3/2009 | Barbu et al. | |

* cited by examiner

*Primary Examiner* — Seyed Azarian

(57) ABSTRACT

A method and system for detecting and modeling a catheter in a fluoroscopic image is disclosed. Catheter tip candidates and catheter body candidates are detected in the fluoroscopic image. One of a plurality of trained shape models is fitted to the catheter tip candidates and the catheter body candidates in order to model a shape of the catheter in the fluoroscopic image.

21 Claims, 7 Drawing Sheets

SHAPE MODELING AND DETECTION OF CATHETER

This application claims the benefit of U.S. Provisional Application No. 61/346,196, filed May 19, 2010, the disclosure of which is incorporated herein by reference.

BACKGROUND OF THE INVENTION

The present invention relates to fluoroscopic imaging, and more particularly, to the detection and modeling of a catheter within fluoroscopic image sequences.

The detection of catheters is important in a variety of medical applications. Catheters are tubes that may be inserted into a body cavity, duct, or vessel. Some types of catheter may be used to generate an electrical map of a heart to assist medical professionals in identifying locations of abnormal electrical activity within the heart. These types of catheters may be inserted into arteries and guided to the heart. Medical procedures using catheters are typically monitored using fluoroscopic imaging, in which a sequence of fluoroscopic images is acquired in real-time during the procedure. The detection of catheters in such fluoroscopic images is difficult due to varying imaging quality of the fluoroscopic images.

BRIEF SUMMARY OF THE INVENTION

The present invention provides a method and system for detecting and modeling a catheter in a fluoroscopic image. Catheter tip candidates and catheter body candidates are detected in the fluoroscopic image. One of a plurality of trained shape models is fitted to the catheter tip candidates and the catheter body candidates.

In an embodiment of the present invention, fitting one of the plurality of trained shape models to the catheter tip candidates and the catheter body candidates includes calculating a probability of each of the plurality of trained shape models. The probability represents the likelihood of each respective trained shape model matching the catheter tip candidates and the catheter body candidates.

In an embodiment of the present invention, the plurality of trained shape models are grouped into a plurality of clusters. Fitting one of the plurality of trained shape models to the catheter tip candidates and the catheter body candidates can include selecting one of the clusters that best matches the catheter tip candidates and the catheter body candidates, and selecting one of the trained shape models of the selected cluster that best matches the catheter tip candidates and the catheter body candidates. A general planar curve corresponding to the selected one of the plurality of trained shape models may be determined. The trained shape models and general planar curve are trained based on annotated training data.

In an embodiment of the present invention, the trained shape model is fitted in a learned subspace detected using principle component analysis to reduce parameters associated with the trained shape models.

In an embodiment of the present invention, the detection of catheter tip candidates is performed by a first classifier trained using a Probabilistic Boosting Tree and detection of catheter body candidates is performed by a second classifier trained using a Probabilistic Boosting Tree.

In an embodiment of the present invention, the catheter body candidates are detected based upon the positions of the catheter tip candidates within the fluoroscopic image.

In an embodiment of the present invention, the fluoroscopic image is one of a plurality of fluoroscopic images in a fluoroscopic image sequence.

These and other advantages of the invention will be apparent to those of ordinary skill in the art by reference to the following detailed description and the accompanying drawings.

DETAILED DESCRIPTION

The present invention is directed to a method and system for detecting and modeling a catheter in a fluoroscopic image. Embodiments of the present invention are described herein to provide a visual understanding of the catheter detection and modeling method. A digital image often includes digital representations of objects or shapes. The digital representation of an object is often described herein in terms of identifying and manipulating the objects. Such manipulations are virtual and carried out in the memory or other circuitry/hardware of a computer system. Accordingly, it is to be understood that embodiments of the present invention may be performed within a computer system using data stored within the computer system.

Figure 1:
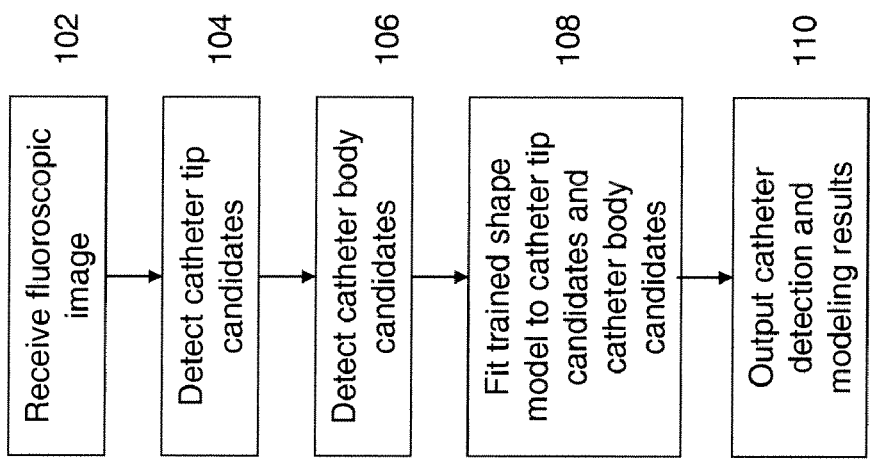
FIG. 1 illustrates a method for detecting and modeling a catheter in a fluoroscopic image according to an embodiment of the present invention.

FIG. 1 illustrates a method for detecting and modeling a catheter in a fluoroscopic image according to an embodiment of the present invention. At step 102, a fluoroscopic image is received. The fluoroscopic image may be a part of a fluoroscopic image sequence, which can be x-ray images taken at a regular time interval while monitoring a heart procedure. The fluoroscopic image can be received directly from an x-ray imaging device or may be loaded on a memory or storage of a computer system or other type of computer readable medium.

Figure 2:
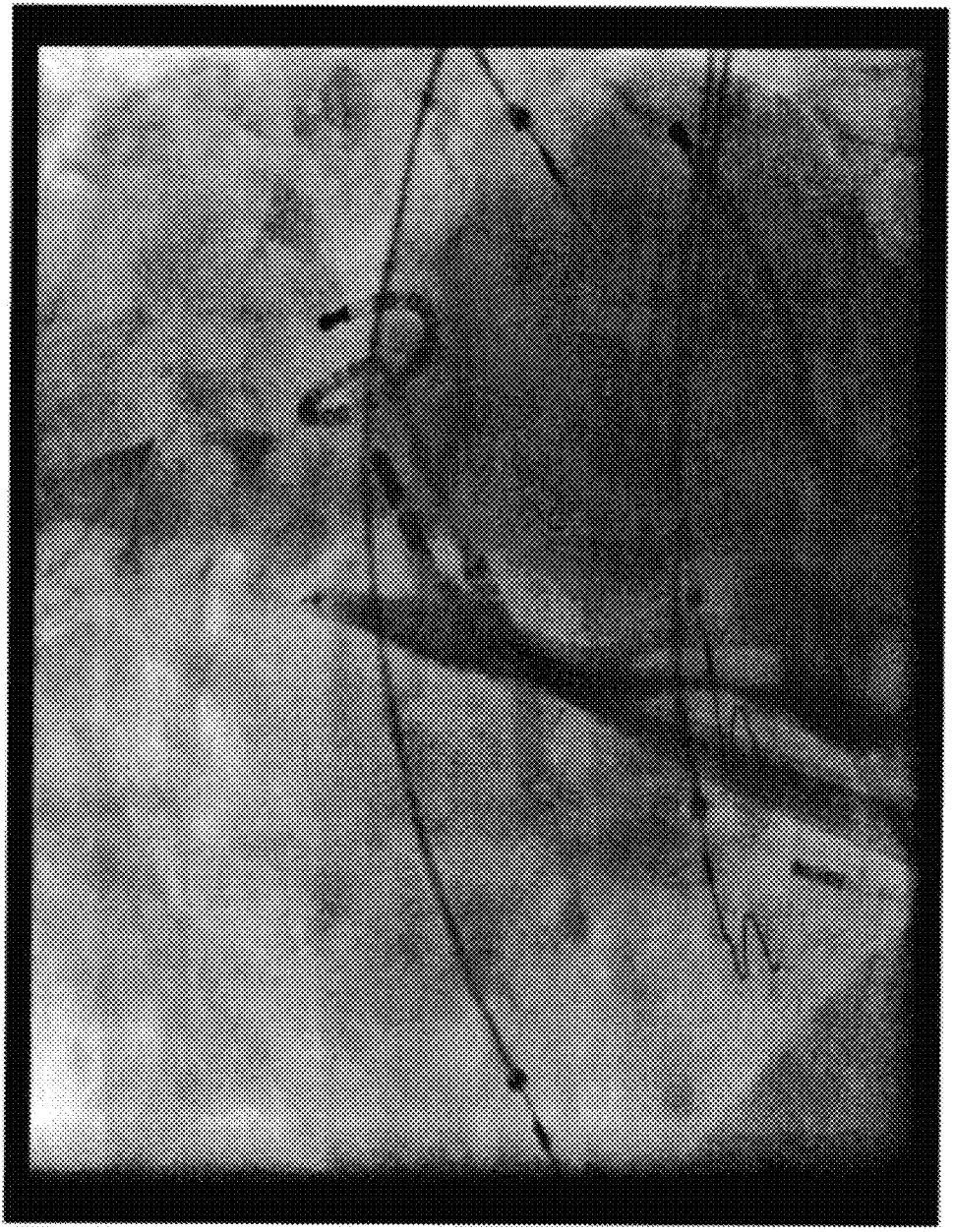
FIG. 2 illustrates an original image of a catheter in a fluoroscopic image.

FIG. 2 illustrates an original image of a catheter in a fluoroscopic image. The original image 202 includes a catheter within the image. Catheter body candidates and catheter tip candidates may be detected based on the method of FIG. 1 described herein, in order to model the catheter included in original image 202.

Returning to FIG. 1, at step 104, catheter tip candidates are detected in the fluoroscopic image. The detection of catheter tip candidates is performed using a catheter tip detector trained based on annotated training data. Detection of the catheter tip candidates by the trained catheter tip detector may be performed using marginal space learning. Marginal space learning is a learning technique where the dimensionality of a search space is gradually increased in order for learning and searching computations to be performed in the sequence of marginal spaces. The sequence of marginal spaces is selected such that the marginal probabilities have small entropies. A classifier is trained at each marginal space learning level in order to detect candidates based on the search space at each level.

At step 106, catheter body candidates are detected in the fluoroscopic image. The detection of the catheter body candidates is performed using a catheter body detector trained based on annotated training data. The catheter body candidates are detected by the trained catheter body detector using marginal space learning. Additionally, the catheter body candidates may also be detected based on their location relative to the catheter tip candidates. That is, a search space for the trained catheter body detector can be constrained based on the detected catheter tip candidates.

A catheter tip point and a catheter body point include three parameters: two for position (x,y) and one for orientation ($\theta$). Two levels of marginal space learning may be used in order to determine candidate parameters for catheter tip candidates and catheter body candidates. In the first level, a classifier is trained to detect candidates based on position. In the second level, a classifier is trained to detect candidates based on position and orientation. Each classifier in the two levels may be trained using a Probabilistic Boosting Tree (PBT) based on training data. The training data includes fluoroscopic images with ground truth catheter tip points and catheter body points annotated therein.

At each marginal space learning level, a PBT classifier may be trained by recursively constructing a tree, where each node of the tree represents a strong classifier. Once each strong classifier is trained, the input training data for the node is classified into two sets, positive and negative. The two new sets are produced to left and right child nodes of each strong classifier node in order to train the child nodes. This represents a recursively constructed PBT which is advantageous for catheter tip candidate and catheter body candidate detection because the appearance of catheter tip points and catheter body points can be clustered into different classes.

Once PBT classifiers are trained for each level, the classifiers are used to detect catheter tip candidates within fluoroscopic images. Accordingly, the catheter tip detector and the catheter body point detector can each include multiple trained classifiers corresponding to the multiple marginal space learning levels. Further detail regarding a method for detecting catheter tip candidates can be found in U.S. Patent Publication No. 2009/0062641, incorporated herein by reference. A similar method can be used for detecting catheter body candidates.

Figure 3:
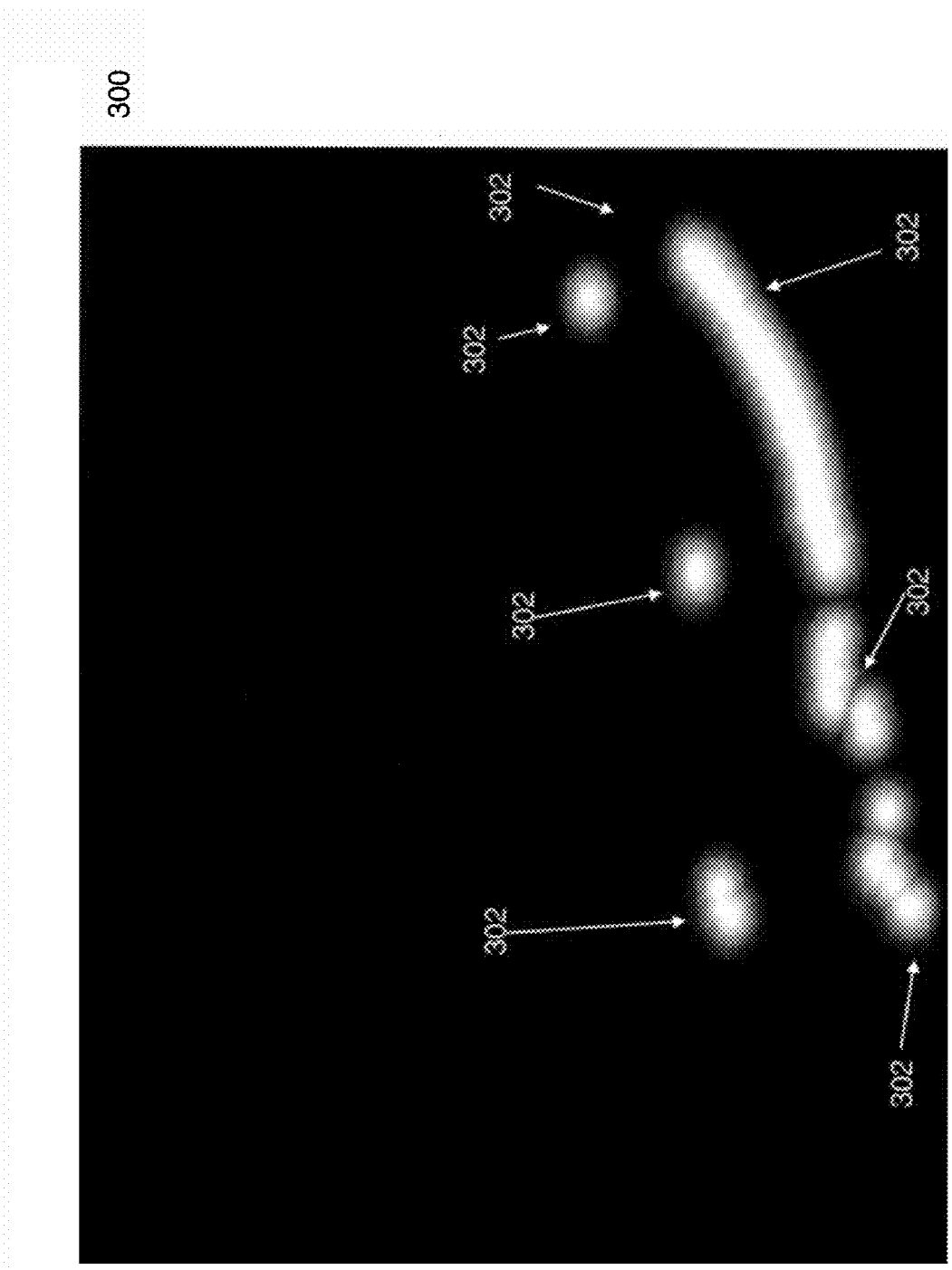
FIG. 3 illustrates a density field showing the catheter body candidates of the catheter detected in the original image 202 shown in FIG. 2.

FIG. 3 illustrates a density field showing the catheter body candidates of the catheter detected in the original image 202 shown in FIG. 2. The density field 302 included in image 300, shows catheter body candidates 304 which have been detected using step 106 described above. Density field 302 including catheter body candidates 304 is used during shape fitting in order to fit a trained shape model to the catheter body candidates.

Returning to FIG. 1, at step 108, a trained shape model is fitted to the catheter tip candidates and the catheter body candidates. The trained shape model represents a model of a catheter corresponding to the detected catheter tip candidates and the detected catheter body candidates found in the fluoroscopic image. The trained shape model is trained in a functional space or subspace of a planar curve. Specifically, the trained shape model is a shape representation of a catheter that is defined to be a directional index function of an arc-length parameterized curve function.

The trained shape model may be a part of set of training data including a plurality of trained shape models. In order to fit the trained shape model to the catheter tip candidates and the catheter body candidates, a probability of each of the trained shape models is calculated. The probability of each trained shape model represents a likelihood of the respective trained shape model matching the catheter tip candidates and the catheter body candidates.

In an advantageous embodiment of the present invention, all of the trained shape models may be grouped into a plurality of clusters. A cluster that best matches the catheter tip candidates and the catheter body candidates is selected. From that cluster, a trained shape model that best matches the catheter tip candidates and the catheter body candidates is selected as the trained shape model for fitting.

In order to further refine the trained shape model that is fitted to the catheter tip candidates and the catheter body candidates, a general planar curve of the trained shape model may be determined. The fitting of the trained shape model may be performed based on a learned subspace detected using principle component analysis in order to reduce parameters associated with the arc-length parameterized curve function of the general planar curve.

In order to perform shape fitting, a training data set including curves representing shape fitted catheters is used. A shape of a planar curve $\alpha(t)=(x(t),y(t))$ can be represented by a direction index function $\theta(s)$. The parameterization function of curve $\alpha(t)$ is represented by $t=g(s)$. For each given different $g(s)$, the planar curve $\alpha(t)$ takes the form $\alpha(g(s))$. In order to remove ambiguity from the parameterization of data, the $g(s)$ is standardized as an arc-length parameterization:

$$s = g^{-1}(t) = \int_0^t \left|\frac{\partial \alpha(t)}{\partial (t)}\right| dt.$$

As a result, $$\frac{\partial \alpha(g(s))}{\partial s} = 1$$

and thus the tangent function of the parameterization curve $\alpha(g(s))$ may be represented as $$\frac{\partial \alpha \circ g^{-1}(s)}{\partial s} = e^{j\theta(s)},$$

where s represents the arc-length parameter. The shape of the planar curve $\alpha(t)$ is represented by the direction index function $\theta(s)$.

Thus, a direction index function $\theta$ is determined for each curve representing a catheter in the training data set discussed above.

For a general planar curve, the functional space of direction index function $\theta(s)$ is the vector space represented by $L^2$.

Within the vector space $L^2$ of $\theta(s)$, principle component analysis is performed in order to reduce the dimension of the vector space by the approximation of three principle components $\{b_1,b_2,b_3\}$ that produce the three largest Eigenvalues. The vector space, or shape space is approximated by a subspace $R^3$ spanned by $\{b_1,b_2,b_3\}$.

The subspace $R^3$ is the subspace in which the shape of the catheter to be modeled resides. In order to determine the subspace $R^3$, the histogram of the distribution of $\theta(s)$ within $R^3$ must be estimated. This estimation is represented by:

$$f_h^1(X) = \frac{1}{nh} \sum_{i=1}^n K\left(\frac{X - X_i}{h}\right),$$

where X represents a coordinate of $\theta(s)$ spanned by $\{b_1,b_2,b_3\}$, $X_i=(<\theta_i,b_1>,<\theta_i,b_2>,<\theta_i,b_3>)$, and K represents a smooth kernel with parameter h. The resulting subspace for the catheter is represented by H, where $$H = \{x \in R^3 \mid f_h^1(x) > \eta\}.$$

The subspace H represents the set of all curves within the training data set. In particular, subspace H includes the estimations of each θ within $R^3$.

Figure 4:
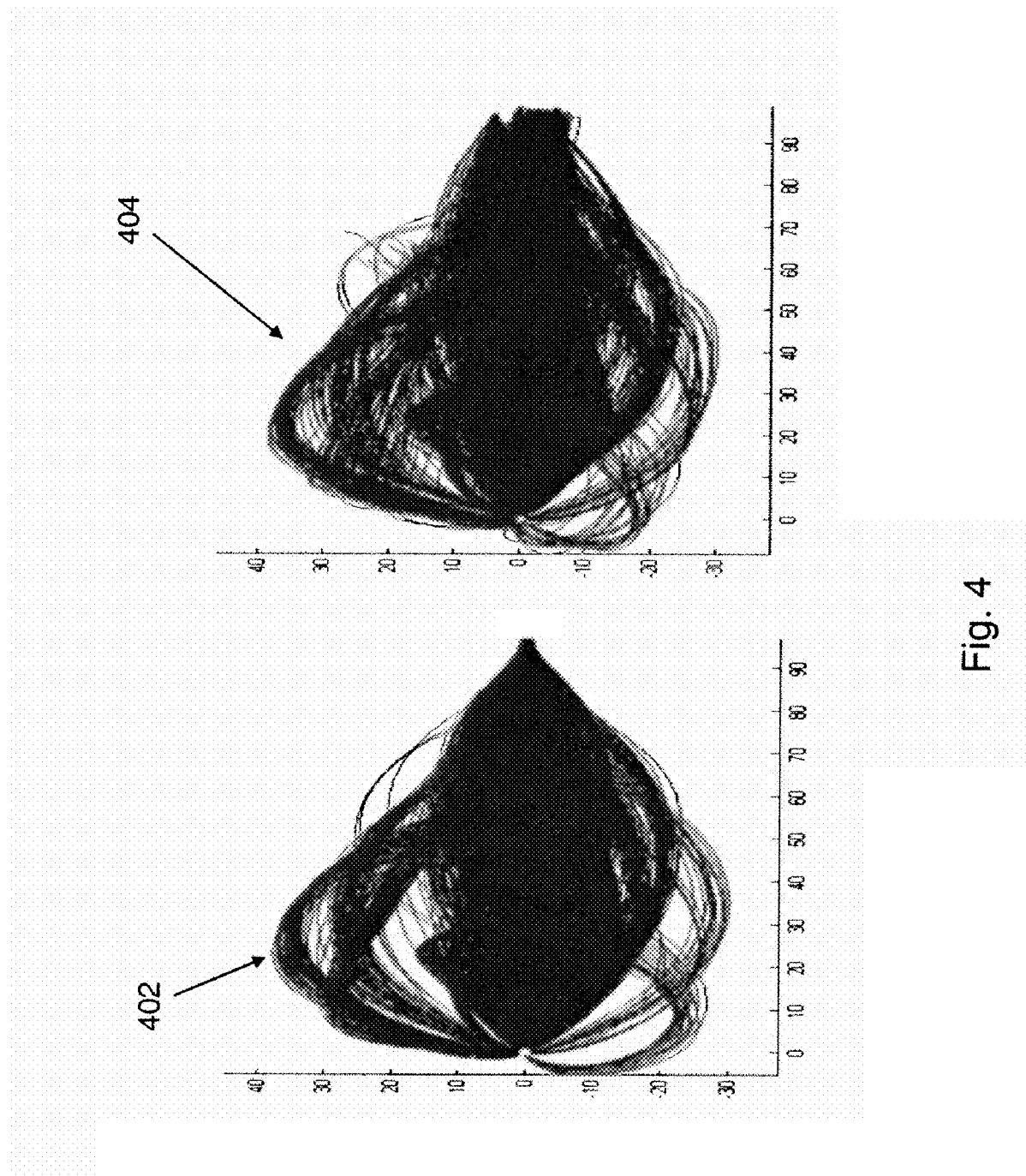
FIG. 4 illustrates an exemplary general planar curve of a shape model and an exemplary approximated general planar curve detected using principle component analysis.

FIG. 4 illustrates an exemplary general planar curve of a shape model and an exemplary approximated general planar curve detected using principle component analysis. General planar curve 402 represents the original general planar curve of a shape model that is to be trained. General planar curve 404 represents the approximated general planar curve of the shape model after using principle component analysis as discussed above.

When fitting a trained shape model to catheter tip candidates and catheter body candidates, $B_i=(x_i,y_i)$ represents the catheter body candidates and $T_i=(x_i,y_i)$ represents the catheter tip candidates. After detection of all catheter body candidates $\{B_i\}_{i=1 \ldots N_B}$ and all catheter tip candidates $\{T_i\}_{i=1 \ldots N_T}$, shape fitting may be performed by determining a coordinate of the shape model within subspace H, X∈H that bests fits with $\{B_i\},\{T_i\}$ under the Euclidean transformation parameters of translation, rotation, and scaling. Thus, the shape model within subspace H that best fits the detected catheter tip candidates and catheter body candidates of the current image is determined.

The curve function may be reconstructed as $$\theta = X^1 b_1 + X^2 b_2 + X^3 b_3$$

$$\alpha_x(s) = \int_0^N e^{j\theta(s)} ds$$

The translation parameter is represented by v∈$R^2$, the rotation parameter is represented by β, and the scale parameter is represented by c. $f_h^2$ represents a 2D density field estimated based on $\{B_i\}$. The shape fitting can be represented as an optimization problem:

$$(X, v, \beta, c) = \arg\max_{X,v,\beta,c} E(X, v, \beta, c).$$

E is an objective function for calculating the appearance of shape α under the Euclidean transformation parameters (c,v,β). E may be defined and represented by:

$$E = \int_0^L f_h^2(cR_\beta(\alpha_x(t) + v))dt,$$

where $$R_\beta = \begin{pmatrix} \cos\beta & -\sin\beta \\ \sin\beta & \cos\beta \end{pmatrix}$$

and L represents the total length of the curve.

In order to solve the objective function described above, a search of the parameter space (X,v,β,c) is required. A heirarchical fitting is performed using a two layer greedy search in the parameter space. The parameter (v,β,c) is restricted to a subspace.

Grouping a plurality of trained shape models into a plurality of clusters, as discussed above with respect to the method of FIG. 1, may also be advantageous and result in a more robust shape fitting. In order to develop a coarse to fine representation of the subspace H, a K-mean algorithm is applied to H. Letting $\{C_i\}_{i=1 \ldots N_C}$ represent a center set of each cluster C, and letting $\{m^i_j\}_{j=1 \ldots N_m^i}$ represent each corresponding member of $\{C_i\}_{i=1 \ldots N_C}$, the subspace is represented coarsely by $\{C_i\}_{i=1 \ldots N_C}$. For a given $C_i$, the cluster is finely represented by $\{m^i_j\}_{j=1 \ldots N_m^i}$.

Once each cluster is represented, a searching space is defined in order to determine the best cluster. In the first search layer, the searching space is defined as $$Z_1 = \{C_i\}_{i=1 \ldots N_C}.$$

The optimization result, representing the best cluster, is $$(\overline{X}, \overline{v}, \overline{\beta}, \overline{c}) = \arg\max_{X \in Z_1, v, \beta, c} E(x, v, \beta, c).$$

In the second search layer, the result is refined within the cluster center at $\overline{X}$ and thus $$Z_2 = \{m^i_j\}_{j=1 \ldots N_m^i}$$

and (v,β,c) is searched within a small open ball center at $(\overline{v},\overline{\beta},\overline{c})$ with radian ε, where $D_\epsilon(v,\beta,c)$ and $$(X, v, \beta, c) = \arg\max_{X \in Z_2, v, \beta, c \in D_\epsilon(\overline{v},\overline{\beta},\overline{c})} E(x, v, \beta, c).$$

Thus, based on the second search layer, the best curve within the cluster can be found. The best curve may then be shape fitted to the catheter body candidates and the catheter tip candidates.

At step 110, the catheter detection and modeling results are output. For example, catheter detection and modeling results can be displayed on a display device of a computer system implementing the method, or can be stored on memory, storage, or a computer readable medium.

Figure 5:
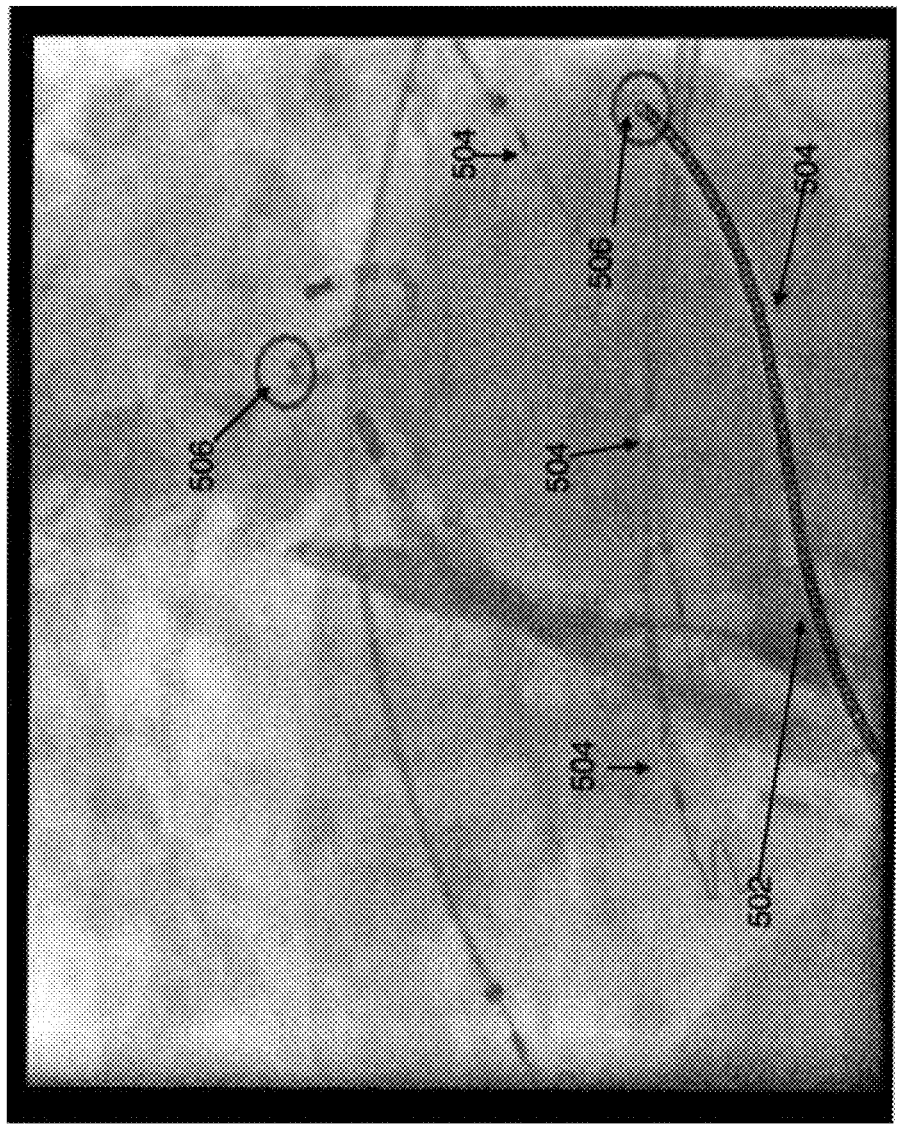
FIG. 5 illustrates an image of a catheter after shape fitting.

FIG. 5 illustrates an image of a catheter after shape fitting. The planar curve generated by the shape fitting described above and in connection with the method of FIG. 1 is shown by the curve 502. The detected catheter body candidates are represented by points 504 and the detected catheter tip candidates are represented by points 506. It is understood that not all of the detected catheter body candidates 504 and catheter tip candidates 506 correspond to the detected curve 502. However, in determining the proper curve 502 to be fitted to all of the detected catheter tip candidates 506 and catheter body candidates 504, all catheter tip candidates 506 and catheter body candidates 504 are shown in FIG. 5 to illustrate how shape fitting is performed.

Figure 6:
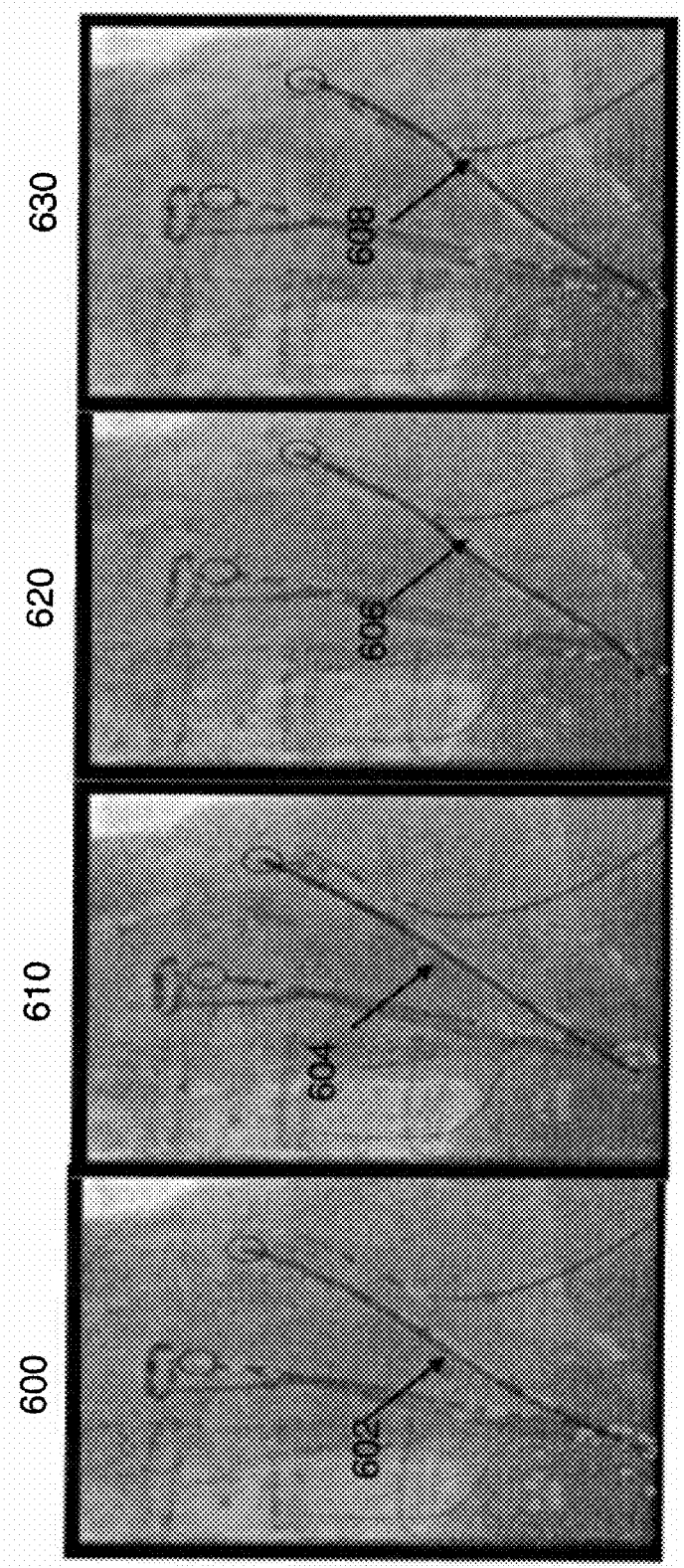
FIG. 6 illustrates an exemplary sequence of fluoroscopic images showing a catheter that has been detected in each fluoroscopic image using the method of FIG. 1.

FIG. 6 illustrates an exemplary sequence of fluoroscopic images showing a catheter that has been detected in each fluoroscopic image using the method of FIG. 1. For example, a shape fitted catheter curve 602 is detected and shown in image 600. The method of FIG. 1 may also be applied to each of fluoroscopic images 610, 620, and 630 shown in FIG. 6. The shape fitted catheter curves corresponding to images 610, 620, and 630 are represented by curves 604, 606, and 608, respectively.

Figure 7:
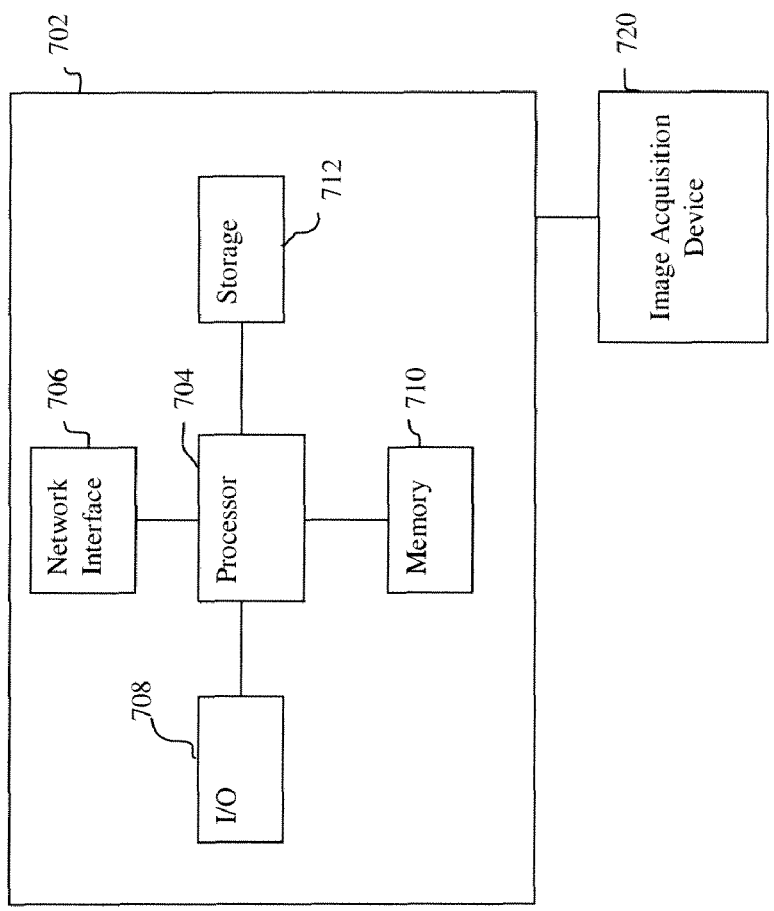
FIG. 7 is a high-level block diagram of a computer capable of implementing the embodiments of the present invention.

The above-described methods for detecting and modeling a catheter may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions, which define such operation. The computer program instructions may be stored in a storage device 712, or other computer readable medium, (e.g., magnetic disk) and loaded into memory 710 when execution of the computer program instructions is desired. Thus, all method steps described above, including the method steps illustrated in FIG. 1, may be defined by the computer program instructions stored in the memory 710 and/or storage 712 and controlled by the processor 704 executing the computer program instructions. An image acquisition device 720, such as a C-arm image acquisition device, can be connected to the computer 702 to input fluoroscopic image sequences to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.) One skilled in the art will recognize that an implementation of an actual computer could contain other components as well, and that FIG. 7 is a high level representation of some of the components of such a computer for illustrative purposes. In addition, computer 702 may also perform other functionalities, such as those described above in connection with FIGS. 2 through 6.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for detecting and modeling a catheter in a fluoroscopic image, comprising:
    detecting catheter tip candidates in the fluoroscopic image;
    detecting catheter body candidates in the fluoroscopic image; and
    fitting one of a plurality of trained shape models to the catheter tip candidates and the catheter body candidates by calculating a probability of each of the plurality of trained shape models, the probability representing the likelihood of the respective trained shape model matching the catheter tip candidates and the catheter body candidates.

2. The method of claim 1, wherein the plurality of trained shape models are grouped into a plurality of clusters and fitting one of a plurality of trained shape models to the catheter tip candidates and the catheter body candidates comprises:
    selecting one of the clusters that best matches the catheter tip candidates and the catheter body candidates; and
    selecting one of the trained shape models of the selected cluster that best matches the catheter tip candidates and the catheter body candidates.

3. The method of claim 2, further comprising:
    determining a general planar curve corresponding to the selected one of the plurality of trained shape models, wherein the trained shape models and general planar curve are trained based on annotated training data.

4. The method of claim 1, further comprising:
    fitting the trained shape model in a learned subspace detected using principle component analysis to reduce parameters associated with the trained shape models.

5. The method of claim 1, wherein detecting catheter tip candidates is performed by a first classifier trained using a Probabilistic Boosting Tree and detecting catheter body candidates is performed by a second classifier trained using a Probabilistic Boosting Tree.

6. The method of claim 1, wherein detecting catheter body candidates is based upon positions of the catheter tip candidates within the fluoroscopic image.

7. The method of claim 1, wherein the fluoroscopic image is one of a plurality of fluoroscopic images in a fluoroscopic image sequence.

8. A system for detecting and modeling a catheter in a fluoroscopic image, comprising:
    means for detecting catheter tip candidates in the fluoroscopic image;
    means for detecting catheter body candidates in the fluoroscopic image; and
    means for fitting one of a plurality of trained shape models to the catheter tip candidates and the catheter body candidates by calculating a probability of each of the plurality of trained shape models, the probability representing the likelihood of the respective trained shape model matching the catheter tip candidates and the catheter body candidates.

9. The system of claim 8, wherein the plurality of trained shape models are grouped into a plurality of clusters and means for fitting one of a plurality of trained shape models to the catheter tip candidates and the catheter body candidates comprises:
    means for selecting one of the clusters that best matches the catheter tip candidates and the catheter body candidates; and
    means for selecting one of the trained shape models of the selected cluster that best matches the catheter tip candidates and the catheter body candidates.

10. The system of claim 9, further comprising:
    means for determining a general planar curve corresponding to the selected one of the plurality of trained shape models,
    means for wherein the trained shape models and general planar curve are trained based on annotated training data.

11. The system of claim 8, further comprising:
    means for fitting the trained shape model in a learned subspace detected using principle component analysis to reduce parameters associated with the trained shape models.

12. The system of claim 8, wherein means for detecting catheter tip candidates comprises a first classifier trained using a Probabilistic Boosting Tree and means for detecting catheter body candidates comprises a second classifier trained using a Probabilistic Boosting Tree.

13. The system of claim 8, wherein means for detecting catheter body candidates uses positions of the catheter tip candidates within the fluoroscopic image.

14. The system of claim 8, wherein the fluoroscopic image is one of a plurality of fluoroscopic images in a fluoroscopic image sequence.

15. A computer readable medium encoded with computer program instructions for detecting and modeling a catheter in a fluoroscopic image, the computer program instructions defining the steps comprising:
    detecting catheter tip candidates in the fluoroscopic image;
    detecting catheter body candidates in the fluoroscopic image; and
    fitting one of a plurality of trained shape models to the catheter tip candidates and the catheter body candidates by calculating a probability of each of the plurality of trained shape models, the probability representing the likelihood of the respective trained shape model matching the catheter tip candidates and the catheter body candidates.

16. The computer readable medium of claim 15, wherein the plurality of trained shape models are grouped into a plurality of clusters and the instructions defining the step of fitting one of a plurality of trained shape models to the catheter tip candidates and the catheter body candidates comprises the steps of:
    selecting one of the clusters that best matches the catheter tip candidates and the catheter body candidates; and
    selecting one of the trained shape models of the selected cluster that best matches the catheter tip candidates and the catheter body candidates.

17. The computer readable medium of claim 16, wherein the instructions further define the step comprising:
    determining a general planar curve corresponding to the selected one of the plurality of trained shape models,
    wherein the trained shape models and general planar curve are trained based on annotated training data.

18. The computer readable medium of claim 15, wherein the instructions further define the step comprising:
    fitting the trained shape model in a learned subspace detected using principle component analysis to reduce parameters associated with the trained shape models.

19. The computer readable medium of claim 15, wherein detecting catheter tip candidates is performed by a first classifier trained using a Probabilistic Boosting Tree and the instructions defining the step of detecting catheter body candidates is performed by a second classifier trained using a Probabilistic Boosting Tree.

20. The computer readable medium of claim 15, wherein detecting catheter body candidates is based upon positions of the catheter tip candidates within the fluoroscopic image.

21. The computer readable medium of claim 15, wherein the fluoroscopic image is one of a plurality of fluoroscopic images in a fluoroscopic image sequence.

* * * * *